US006929606B2

(12) United States Patent
Ritland (10) Patent No.: US 6,929,606 B2
(45) Date of Patent: Aug. 16, 2005

(54) RETRACTOR AND METHOD FOR SPINAL PEDICLE SCREW PLACEMENT

(75) Inventor: Stephen Ritland, Flagstaff, AZ (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

(21) Appl. No.: 10/437,560

(22) Filed: May 13, 2003

(65) Prior Publication Data

US 2003/0236447 A1 Dec. 25, 2003

Related U.S. Application Data

(63) Continuation-in-part of application No. 10/060,905, filed on Jan. 29, 2002.
(60) Provisional application No. 60/380,345, filed on May 13, 2002, and provisional application No. 60/264,943, filed on Jan. 29, 2001.

(51) Int. Cl.[7] .............................. A61B 1/32; A61F 2/46
(52) U.S. Cl. ...................... 600/201; 600/210; 606/96; 606/99
(58) Field of Search ................................ 600/201, 205, 600/217, 210; 606/96, 97, 99

(56) References Cited

U.S. PATENT DOCUMENTS

| | | |
|---|---|---|
| 569,839 A | 10/1896 | Roeloffs |
| 3,470,872 A | 10/1969 | Grieshaber |
| 3,875,595 A | 4/1975 | Froning |
| 4,232,660 A | 11/1980 | Coles |
| 4,440,168 A | 4/1984 | Warren |
| 4,481,947 A | 11/1984 | Chester ..................... 126/303 |
| 4,545,374 A | 10/1985 | Jacobson |
| 4,573,448 A | 3/1986 | Kambin |
| 4,617,922 A | 10/1986 | Griggs .................. 128/92 YS |
| 4,620,460 A | 11/1986 | Gonzales, Jr. |
| 4,686,972 A | 8/1987 | Kurland |
| 4,736,738 A | 4/1988 | Lipovsek |
| 4,747,394 A | 5/1988 | Watanabe ..................... 128/20 |
| 4,798,111 A | 1/1989 | Cheeseman |

(Continued)

FOREIGN PATENT DOCUMENTS

| | | |
|---|---|---|
| WO | WO 00/18306 A1 | 4/2000 |
| WO | WO 02/060330 A1 | 8/2002 |

OTHER PUBLICATIONS

Wolfhard Caspar, *Technique of Microsurgery*, in Microsurgery of the Lumbar Spine: Principles and Techniques in Spine Surgery 105–122 (Aspen Publications, 1990).

Kambin, Parviz, "Arthroscopic Microdiscectomy: Minimal Intervention in Spinal Surgery", National Library of Medicine, 1991 p 67–100, Urban & Schwarzenberg.

Schaffer, Johnathan et al., "Percutaneous Posterolateral Lumbar Discectomy and decompression with a 6.9 Millimeter Cannula", The Journal of Bone and Joint Surgery, 1991, pp 822–831.

(Continued)

*Primary Examiner*—Cary E. O'Connor
(74) *Attorney, Agent, or Firm*—Nutter, McClennen & Fish LLP (57) ABSTRACT

To avoid traditional muscle dissection required in the placement of a screw for a pedicle screw fixation, a retractor is provided having a guide of an appropriate length to provide access from the skin surface to the dorsal aspect of the vertebra over the pedicle. The retractor has a handle to provide appropriate holding leverage and to maintain the guide so as to stabilize the guide against the lateral aspects of the facet with the paraspinous musculature. The retractor has a channel of an appropriate size to accommodate a variety of tools, including a drill bit or a tap. The channel also provides a pathway for a probe or feeler to inspect the placement of the screw. A tool groove may be provided in the channel to support the shaft of a tool, such as a tap.

21 Claims, 9 Drawing Sheets

U.S. PATENT DOCUMENTS

| | | | |
|---|---|---|---|
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeeley | |
| 5,035,232 A | 7/1991 | Lutze et al. | 128/20 |
| 5,048,379 A | 9/1991 | Gramera | |
| 5,052,373 A | 10/1991 | Michelson | 128/20 |
| 5,084,043 A | 1/1992 | Hertzmann | |
| 5,098,435 A | 3/1992 | Stednitz | |
| 5,106,376 A | 4/1992 | Mononen | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,195,541 A | 3/1993 | Obenchain | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | 128/20 |
| 5,312,360 A | 5/1994 | Behl | |
| 5,356,413 A | 10/1994 | Martins et al. | |
| 5,363,841 A | 11/1994 | Coker | |
| 5,431,639 A | 7/1995 | Shaw | |
| 5,431,651 A | 7/1995 | Goble | |
| D361,381 S | 8/1995 | Koros et al. | D24/135 |
| 5,439,464 A | 8/1995 | Shapiro | |
| 5,472,426 A | 12/1995 | Bonati | |
| 5,489,274 A | 2/1996 | Chu | |
| 5,512,038 A | 4/1996 | O'Neal et al. | 600/210 |
| 5,601,550 A | 2/1997 | Esser | 606/54 |
| 5,611,778 A | 3/1997 | Brinon | |
| 5,687,739 A | 11/1997 | McPherson | |
| 5,716,415 A | 2/1998 | Steffee | 623/17 |
| 5,743,853 A | 4/1998 | Lauderdale | |
| 5,746,720 A | 5/1998 | Stouder, Jr. | |
| 5,766,221 A | 6/1998 | Benderev et al. | 606/232 |
| 5,792,044 A | 8/1998 | Foley | |
| D399,955 S | 10/1998 | Koros et al. | D24/135 |
| 5,816,257 A | 10/1998 | Chin | |
| RE36,020 E | 12/1998 | Moore | |
| 5,851,207 A | 12/1998 | Cesarone | |
| 5,882,344 A | 3/1999 | Stouder, Jr. | |
| 5,885,300 A | 3/1999 | Tokuhashi et al. | 606/99 |
| 5,891,147 A | 4/1999 | Moskovitz et al. | 606/79 |
| 5,895,352 A | 4/1999 | Kleiner | 600/206 |
| 5,895,390 A | 4/1999 | Moran et al. | 606/96 |
| 5,897,593 A | 4/1999 | Kohrs et al. | 623/17 |
| 5,899,901 A | 5/1999 | Middleton | |
| 5,902,231 A | 5/1999 | Foley | |
| 5,913,818 A * | 6/1999 | Co et al. | 600/204 |
| 5,928,139 A | 7/1999 | Koros | |
| 5,944,658 A | 8/1999 | Koros et al. | 600/232 |
| 5,954,635 A | 9/1999 | Foley | |
| 5,954,671 A | 9/1999 | O'Neill | |
| 5,967,970 A | 10/1999 | Cowan | |
| 5,971,920 A | 10/1999 | Nagel | |
| 5,976,146 A | 11/1999 | Ogawa | |
| 5,996,447 A | 12/1999 | Bayouth | |
| 6,007,487 A * | 12/1999 | Foley et al. | 600/235 |
| 6,010,520 A | 1/2000 | Pattison | |
| 6,063,088 A * | 5/2000 | Winslow | 606/61 |
| 6,080,155 A | 6/2000 | Michelson | 606/61 |
| 6,081,741 A | 6/2000 | Hollis | |
| 6,083,225 A | 7/2000 | Winslow et al. | 606/61 |
| 6,113,602 A | 9/2000 | Sand | 606/61 |
| 6,120,434 A | 9/2000 | Kimura | |
| 6,120,506 A | 9/2000 | Kohrs et al. | 606/80 |
| D433,296 S | 11/2000 | Yamakawa | |
| 6,152,871 A | 11/2000 | Foley | |
| 6,156,006 A | 12/2000 | Brosens | |
| 6,159,179 A | 12/2000 | Simonson | |
| 6,162,170 A | 12/2000 | Foley | |
| 6,162,236 A | 12/2000 | Osada | |
| D436,513 S | 1/2001 | Yamakawa | |
| 6,176,823 B1 | 1/2001 | Foley | |
| D438,074 S | 2/2001 | Marr | |
| 6,197,002 B1 | 3/2001 | Peterson | |
| 6,206,822 B1 | 3/2001 | Foley | |
| 6,206,826 B1 | 3/2001 | Mathews et al. | 600/210 |
| 6,206,885 B1 | 3/2001 | Ghahremani et al. | 606/96 |
| 6,214,004 B1 | 4/2001 | Coker | |
| 6,217,509 B1 | 4/2001 | Foley | |
| 6,224,597 B1 | 5/2001 | Coker | |
| 6,224,608 B1 | 5/2001 | Ciccolella | |
| 6,245,072 B1 | 6/2001 | Zdeblick et al. | 606/61 |
| 6,258,097 B1 | 7/2001 | Cook | |
| 6,267,763 B1 | 7/2001 | Castro | 606/61 |
| 6,270,498 B1 | 8/2001 | Michelson | 606/61 |
| 6,283,966 B1 | 9/2001 | Houfburg | |
| 6,287,313 B1 | 9/2001 | Sasso | |
| 6,296,609 B1 | 10/2001 | Brau | |
| 6,312,432 B1 | 11/2001 | Leppelmeier | |
| 6,342,057 B1 | 1/2002 | Brace | |
| 6,348,058 B1 * | 2/2002 | Melkent et al. | 606/130 |
| 6,354,176 B1 | 3/2002 | Nordlin | |
| 6,371,959 B1 | 4/2002 | Trice | |
| 6,371,968 B1 | 4/2002 | Kogasaka | |
| 6,418,821 B1 | 7/2002 | Yamakawa | |
| 6,428,472 B1 | 8/2002 | Haas | 600/206 |
| 6,461,330 B1 | 10/2002 | Miyagi | |
| D466,766 S | 12/2002 | Marty | |
| 6,520,907 B1 | 2/2003 | Foley | |
| 6,524,238 B2 * | 2/2003 | Velikaris et al. | 600/213 |
| 6,530,926 B1 | 3/2003 | Davison | |
| 6,540,756 B1 | 4/2003 | Vaughan | |
| 6,692,434 B2 | 2/2004 | Ritland | |
| 2001/0012942 A1 | 8/2001 | Estes | |
| 2001/0027320 A1 | 10/2001 | Sasso | |
| 2002/0011135 A1 | 1/2002 | Hall | |
| 2002/0016592 A1 | 2/2002 | Branch | |
| 2002/0022764 A1 | 2/2002 | Smith | |
| 2002/0049368 A1 | 4/2002 | Ritland | |
| 2002/0058948 A1 | 5/2002 | Arlettaz | |
| 2002/0077632 A1 | 6/2002 | Tsou | |
| 2002/0082695 A1 | 6/2002 | Neumann | |
| 2002/0143235 A1 | 10/2002 | Pagliuca | |
| 2003/0083688 A1 | 5/2003 | Simonson | |
| 2003/0083689 A1 | 5/2003 | Simonson | |
| 2003/0187431 A1 | 10/2003 | Simonson | |
| 2003/0220689 A1 | 11/2003 | Ritland | |
| 2003/0236447 A1 | 12/2003 | Ritland | |
| 2004/0106997 A1 | 6/2004 | Lieberson | |

OTHER PUBLICATIONS

Savitz, Martin, "Same–Day Microsurgical Arthroscopic Latera–Approach Laser–Assisted (SMALL) Fluoroscopic Discectomy", Journal of Neurosurgery; Jun. 1994, pp 1039–1045.

Kambin, Parviz, "Percutaneous Posterolateral Discectomy", Clinical Orthopaedics and Related Research, Section II, pp 145–154.

Hilton, Donald et al., "Medtronic Sofamor Danek METR Microdiscectomy Surgical Technique Brochure",2001.

Wiltse, "New Uses and Refinements of the Paraspinal Approach to the Lumbar Spine", Spine, vol. 13 No. 6 1988, pp. 696–706.

U.S. Appl. No. 10/165,991, filed Jun. 10, 2002, Simonson.

U.S. Appl. No. 10/899,707, filed Jul. 26, 2004, Simonson.

Sofamor Danek, "MED MicroEndoscopic Discectomy System" (1997).

Web pages, http://www.brainlab.com, Apr. 2, 2002.

* cited by examiner

Fig_8

Fig_7

FIG. 15

RETRACTOR AND METHOD FOR SPINAL PEDICLE SCREW PLACEMENT

CROSS-REFERENCE TO RELATED APPLICATIONS

This application is a continuation-in-part of U.S. application Ser. No. 10/060,905 filed Jan. 29, 2002 pending, entitled "Retractor And Method For Spinal Pedicle Screw Placement" which claimed priority from U.S. Provisional Patent Application No. 60/264,943 filed Jan. 29, 2001 entitled "Retractor And Method For Spinal Pedicle Screw Placement", and this application also claims priority from U.S. Provisional Patent Application No. 60/380,345 filed May 13, 2002 entitled "Retractor and Method for Spinal Pedicle Screw Placement" all of which are incorporated herein by reference in their entireties.

FIELD OF THE INVENTION

The present invention is directed to a novel retractor and a method using such retractor for placing spinal pedicle screws.

SUMMARY OF THE INVENTION

Pedicle screw fixation has become an important part of stabilizing the spine to assist in arthrodesis. Traditionally a significant amount of muscle dissection has been required to prepare for screw placement. Recently, various approaches have been developed to minimize unnecessary disturbance of paraspinous structures while still accomplishing satisfactory fixation of the spine and the concomitant grafting necessary to achieve arthrodesis.

The retractor of the present invention eases intermuscular placement of pedicle screws by providing a minimally invasive approach, and specifically lends itself to image guided applications. The characteristics of the retractor are described below with accompanying figures to illustrate the features.

The retractor's guide channel is of an appropriate length to provide access from the skin surface to the dorsal aspect of the vertebra over the pedicle. The handle of the retractor is attached to provide appropriate holding leverage to maintain the position of the retractor and to stabilize its guide portion against the lateral aspect of the facet with the paraspinous musculature.

An elongated insert may be placed within the guide channel of the retractor. The insert provides a working channel or hollow bore of an appropriate size to accommodate various instruments. For example, the working channel may receive an awl or perforator for the bony cortex, a drill for the pedicle if desired, or a tap for the pedicle and body of the vertebra. The working channel also provides a pathway for a probe or feeler to inspect the placement of the screw. Additionally, the insert may be configured to allow for guided instruments to confirm position of the screw placement. Moreover, attachment of a tracker to the retractor, the insert, or to instruments used through the insert allows coupling of the surgical procedure with an image guided system.

The retractor is configured such that removal of the insert from the guide channel of the retractor provides a protected working channel for placement of the pedicle screw. The tip of the retractor may be textured and obliquely cut to help maintain position of the retractor against the lateral aspect of the facet. The guide channel is preferably open on one side to allow removal of the retractor after placement of the screw. The channel is of sufficient length to maintain muscle retraction necessary for screw placement.

The shape of the distal end of the retractor aids easy placement of the retractor with minimal muscle separation, thus helping to displace soft tissues while placing the retractor and minimizing the tendency of the retractor to catch on soft tissue during entry. Preferably, there are projections and a textured distal surface to help maintain position against the bone and to avoid displacement while working through the retractor. The cutout, preferably semi-circular or curved, at the distal end is of an appropriate size to allow use of a tap and subsequent placement of a pedicle screw.

In a separate aspect of the invention, a retractor including a tool groove is provided, wherein the tool groove is used to assist a surgeon in guiding a tool to the interior surgical work site. The tool groove may occupy only a portion of the length of the guide portion of the retractor, or it may extend the entire length of the guide portion of the retractor.

In yet a separate aspect of the invention, a retractor including a guide wire channel is provided.

Additional advantages of the present invention will become readily apparent from the following discussion, particularly when taken together with the accompanying drawings.

BRIEF DESCRIPTION OF THE DRAWINGS

FIG. 16a is a side elevation view of a separate embodiment of the present invention;

FIG. 16b is a front elevation view of the device shown in FIG. 16a;

FIG. 16c is a cross section of the guide portion of the device of FIG. 16b taken along line 16c—16c;

FIG. 16d is a cross section of the guide portion of the device of FIG. 16b, but with an interior hole and without a side slot;

FIG. 17b is a front elevation view of a dilator for the guide wire shown in FIG. 17a;

DETAILED DESCRIPTION

Figures 1, 1A, 2:
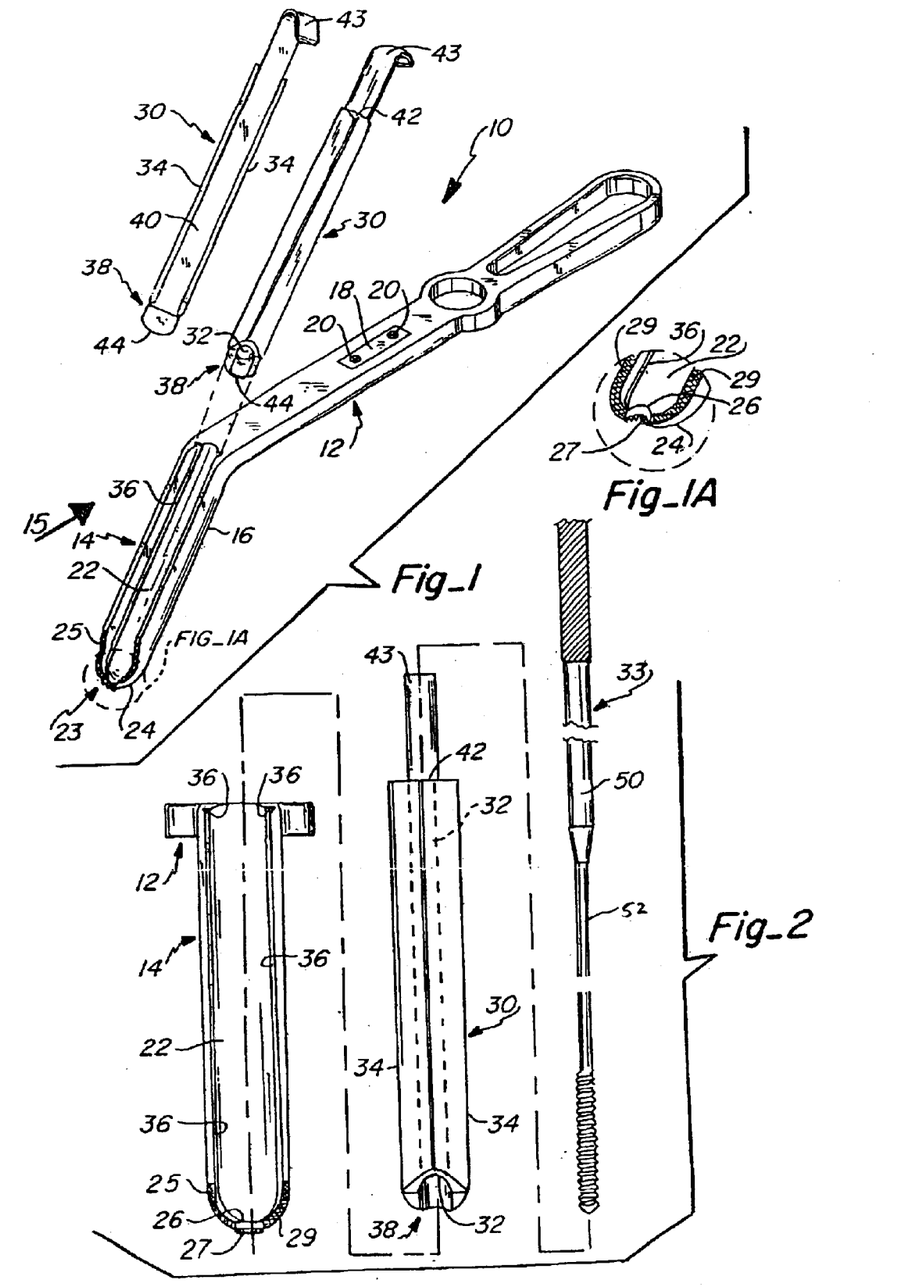
FIG. 1 is a perspective view of one embodiment of the retractor of the present invention, and front and rear views of an embodiment of the insert for the retractor.
FIG. 1a is an enlarged view of the distal end of the retractor.
FIG. 2 is a front elevation view of the retractor of FIG. 1, taken along arrow 15, of one embodiment of the insert for the retractor adapted for use with a surgical tap, and a surgical tap.

With reference to FIG. 1, retractor 10 of the present invention is depicted in a perspective view. Retractor 10 preferably comprises two portions, a handle 12 and a guide portion 14. Handle 12 is attached to the proximal end of guide portion 14. Handle 12 may be of various configurations to allow access to the surgical site while providing a means of gripping the retractor 10 such that sufficient leverage may be applied to maintain the desired orientation of retractor 10 at the surgical site. In a preferred embodiment, handle 12 is oriented at an angle of between about 90 and about 135 degrees from the guide portion 14. Handle 12 may include a slot 18 for interconnecting an attachment or a supplemental handle using handle screws 20. Provision of slot 18 allows for various supplemental handle configurations to be used with retractor 10 to provide different holding leverages, as well as to provide interchangeable geometries that may be desired to overcome spatial constraints imposed by a specific patient's physical attributes. Alternately, an image tracker may be attached to slot 18 as discussed further below.

Guide portion 14 is used for access to the interior of the surgical site. Typically, an incision is made in the patient's skin and muscle. Subsequently, the guide portion 14 is inserted through the exterior portion of the incision to create and maintain access to the interior targeted body part, such as the patient's spine. As described below, specific features of guide portion 14 provide for improved access to the spine.

Guide portion 14 is preferably half-cylinder or U-shaped. More particularly, the rear surface 16 of guide portion 14 is preferably convex when viewing retractor 10 from the rear side of retractor 10. The U-shaped front of guide portion 14 includes a hollow region or guide channel 22. Guide channel 22 extends from the distal end 23 of guide portion 14 up to and including the upper-most or proximal end of guide portion 14. In this manner, guide channel 22 maybe used to guide surgical tools and implants from the exterior of the surgical site down to the interior-most portion of the surgical site by inserting surgical tools down through the guide channel.

The distal end 23 of guide portion 14 includes a rounded tip 24. In addition, the distal end 23 of guide portion 14 is shown as being truncated obliquely along the lower medial face 25 to more closely approximate the lateral aspect of the facet of the paraspinous musculature of the patient, and provide for improved medial positioning of the guide portion 14 for placement of a drill and/or tap into the bony structure of the patient. The rounded tip 24 may further include a cutout or an opening 26 at its end. In a preferred embodiment shown in FIG. 1a, opening 26 is semicircular. One or more projections 27 may be provided around the end-most portion of opening 26 to aid in maintaining the position of the retractor 10 during use by stabilizing retractor 10 against the bony surface of the vertebrae. In addition, texturing such as ridges and grooves or machined points may be placed on the medial surface 29 of the lower medial face 25 of guide portion 14 to further stabilize retractor 10 when in use.

Figures 3, 4, 5, 6:
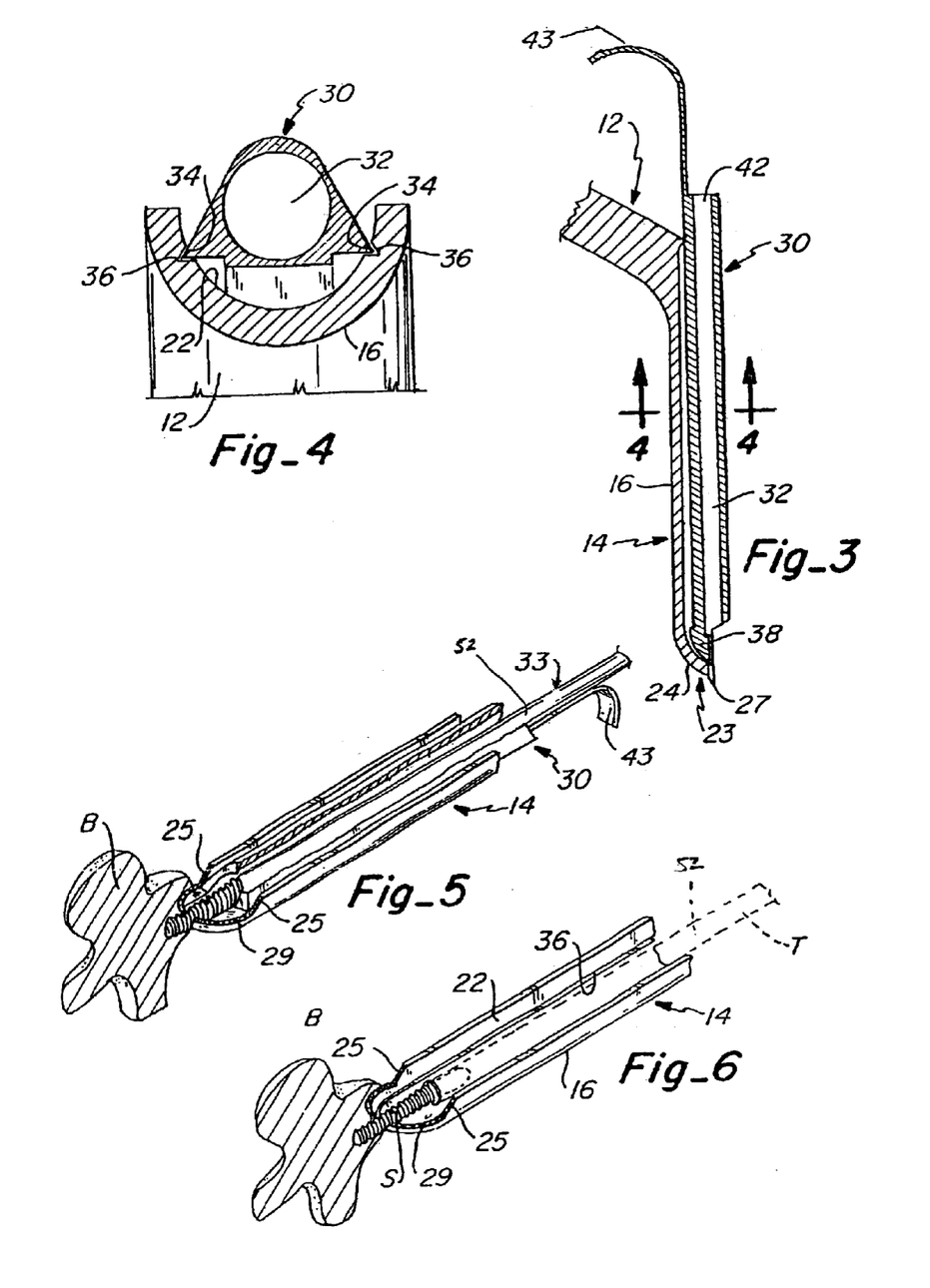
FIG. 3 is a vertical cross-sectional view of the retractor and an insert mounted within the retractor.
FIG. 4 is a horizontal cross-sectional view of the retractor taken along line 4—4 of FIG. 3 and an insert mounted within the retractor.
FIG. 5 is perspective view of the retractor of the present invention during use in a human spine wherein an insert is placed within the retractor and a tap is inserted through the insert.
FIG. 6 is another perspective view of the retractor, with the insert removed and the retractor being used as a guide for emplacement of a pedicle screw.

Referring now also to FIGS. 2 and 4, to aid in facilitating use of tools at the distal end of guide portion 14, an insert 30 may be placed within guide channel 22 to assist the surgeon in guiding and aligning tools along the desired orientation. In a preferred embodiment, insert 30 is generally triangular-shaped and has an aperture or hollow bore 32. Hollow bore 32 allows various tools to be guided down to the targeted area within the surgical site, such as tap 33.

Triangular-shaped insert 30 includes base edges 34. Base edges 34 of insert 30 cooperate with grooves 36 located within guide channel 22 to stabilize insert 30 within guide channel 22. Base edges 34 are simply side projections which mate with the grooves 36. Alternately, in lieu of base edges 34, insert 30 may include one or more discontinuous side projections (not shown). Similar to the base edges 34 of insert 30, these side projections could cooperate with a corresponding number of discontinuous grooves (not shown) located within guide channel 22 to aid in stabilizing insert 30 within guide channel 22.

Insert 30 includes a distal tip 38, a longitudinal shaft 40, a proximal end 42, and an optional handle 43. The distal tip 38 of insert 30 maybe rounded, defining a perimeter edge 44. Perimeter edge 44 cooperates with the lower distal portion of groove 36 within guide channel 22 to further stabilize the distal tip 38 of insert 30, and to further prevent unnecessary entanglement with the patient's bodily tissues when inserting the insert 30 into the guide channel 22.

Referring now to FIGS. 3 and 4, the retractor 10 of the present invention is shown with insert 30 received in the retractor 10. As described above, the base edges 34 of the triangular-shaped insert 30 mate with corresponding grooves 36 in the guide channel 22 of retractor 10. The distal tip 38 of insert 30 mates with the distal end 23 and rounded tip 24 of retractor guide portion 14 such that insert 30 does not extend beyond distal end 23. FIGS. 3 and 4 also depict the hollow bore 32 through which a drill or tap 33 is inserted, thereby guiding the tap 33 to its targeted location.

With reference to FIG. 5, a tap 33 is shown inserted though the bore 32 of the insert 30, and the insert is placed in the guide channel 22 of retractor 10. Tap 33 is used to create an appropriate bore in the bone "B" for receipt of a medical device, such as a pedicle screw "S". Tap 33 may be sized in diameter to restrict passage of the tap 33 beyond a specified length through insert 30. Specifically, tap 33 may contain a larger diameter section 50 which prevents passage of the tap 33 beyond the proximal opening 42 of insert 30.

With reference now to FIG. 6, once the tapping operation is complete, tap 33 and insert 30 may be removed from guide channel 22. Guide channel 22 remains in place and is then used to guide a medical device, in this case, a pedicle screw S. The retractor 10 thus provides for proper alignment of the screw S. Further, the opening 26 in the distal end 23 of guide channel 22 is sized and shaped to accommodate the shank of screw S so that screw S may be properly aligned with the bore created by tap 33. Tool T, such as a medical screwdriver, is then used to finish installation of screw S by screwing screw S into bone B.

Figure 7:
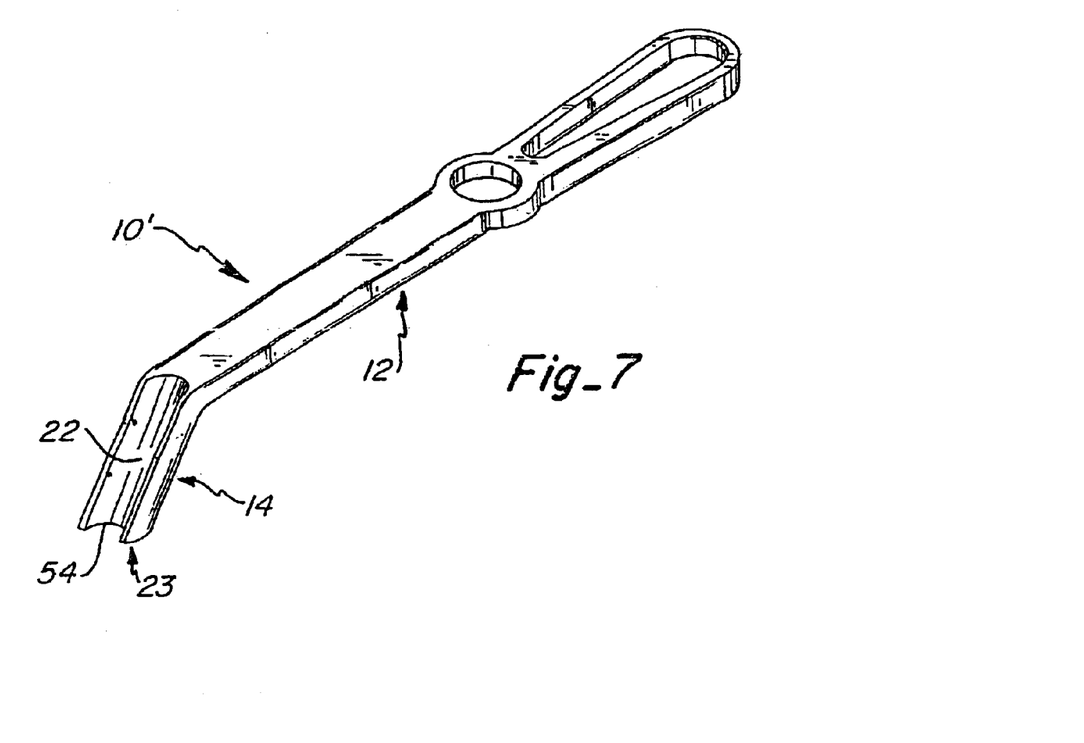
FIG. 7 is a perspective view of a further embodiment of the present invention having a recessed and curved distal tip at its guide portion.

Referring now to FIG. 7, in a further embodiment, a retractor 10' without a rounded tip is illustrated. As shown, the retractor has a recessed and curved distal tip 54. This embodiment offers the advantage of offering a U-shaped guide channel 22; however, a rounded tip is not present to interfere with visibility of the surgical site. The U-shaped guide channel 22 extends from the upper end of guide portion 14 down to the distal end 23 of the guide portion 14. As with the previous embodiment, distal end 23 of the guide portion 14 may be obliquely cut, with optional projections (not shown) formed at the end-most portion of the distal end 23. Additional texturing may also be provided along the medial surface of guide portion 14 to assist with stabilizing retractor 10' against the neighboring area of the surgical site.

Due to the frequently limited amount of exposure of the spine or interior surgical area, the spinal implant procedures lend themselves to use of image guidance for surgery. Examples of such image guidance systems include the BrainLAB System and the Stealth System. As understood by those skilled in the art, these image guidance systems utilize a computer system with a monitor and two cameras that emit infrared signals, thereby determining the patient's position in the operating room as well as the position of the surgical instruments in relation to the patient's spine. The image guidance systems use data from standard CT or MRI scans to build a three dimensional image of the patient's spine. This model is then electronically matched to the patient's anatomy during surgery, allowing the surgeon, in effect, to see through tissue in order to accurately determine the placement of instruments or devices. During the operation, sensitive structures such as blood vessels and nerves, which the surgeon wants to avoid on the way to the anatomical target, can be visualized. In addition, during the operation the surgeon can follow the movements of his or her instruments on the computer screen in real time.

Figure 8:
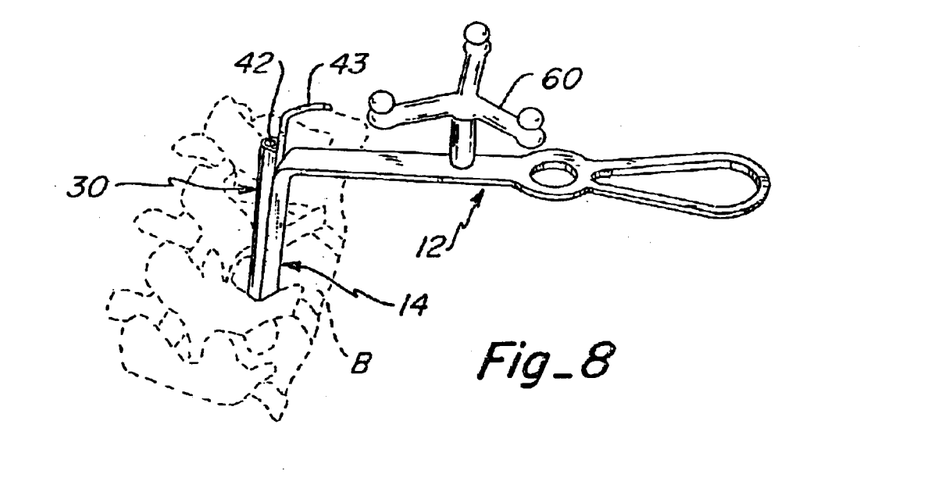
FIG. 8 is a perspective view of the retractor of the present invention fitted with an image tracker on the retractor's handle, shown in simulated application with the human spine.

Referring now to FIG. 8, retractor 10 is shown in one possible relationship with the human spine. The retractor 10 can be positioned at a desired location in relation to spinal processes and maintained in position with the projections 27 and texturing which assist in anchoring the retractor on the patient. The insert 30 may then be used as a guide for subsequent tapping, or like operations. The retractor 10 with insert 30 provides a working channel for tracked instruments. Attachment of a tracker 60 directly to insert 30, or alternately to the retractor handle 12 as shown in FIG. 8, allows a surgeon to guide the guide channel 22 of retractor 10, or hollow bore 32 of insert 30 directly, and thus avoid tracking the instruments themselves, such as a drill or tap 33.

Figures 9, 10:
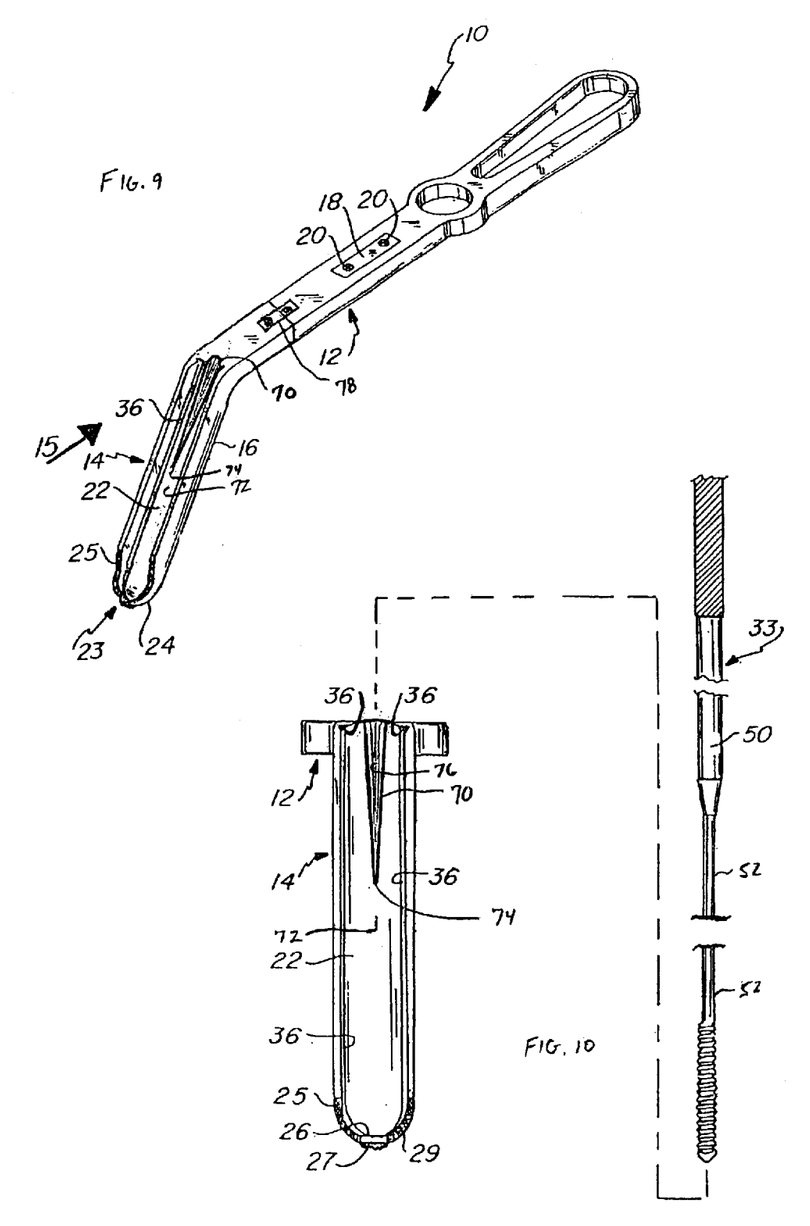
FIG. 9 is a perspective view of a separate embodiment of the present invention having a partial-length tool groove.
FIG. 10 is a front elevation view of the retractor depicted in FIG. 9 along arrow 15.

Referring now to FIG. 9, in yet a separate embodiment, retractor 10 includes a tool groove 70. Tool groove 70 is sized to cradle a surgical tool, such as tap 33, to assist a surgeon in aligning the tap 33 with a desired target location. More particularly, tool groove 70 is a second channel like feature that is formed in the guide channel 22 of guide portion 14. Tool groove 70 may be a partial-length or full-length groove within guide portion 14, as more fully described below.

Referring still to FIG. 9, tool groove 70 may be formed in only a portion of guide portion 14, such as the upper half or upper one-third of guide portion 14. FIG. 10 provides a front elevation view of the embodiment of retractor 10 shown in FIG. 9. The view of FIG. 10 is taken in the general direction of arrow 15 of FIG. 9. FIGS. 9 and 10 illustrate that in one preferred embodiment, tool groove 70 tapers along a portion of the length of guide portion 14, where it terminates at tool groove end 74. More specifically, tool groove 70 may be of a variety of depths set into the interior back surface 72 of guide channel 22 of guide portion 14. For example, tool groove 70 may be relatively shallow near handle 12, such that it cradles only a portion of the shaft of a tool, or it may relatively deep near handle 12, such that it cradles all or nearly all of the circumference of the tool. Furthermore, as shown in FIGS. 9 and 10, tool groove 70 may vary in depth along its length within guide portion 14, such that it essentially terminates at a tool groove end 74 at some point along the length of guide portion 14. In so doing, the back surface 76 of tool groove 70 serves as a guide plane for the shaft 52 of a surgical tool, such as tap 33. The tool groove end 74 may terminate at different locations along the length of guide portion 14, resulting in separate retractors 10 having tool grooves 70 with back surfaces 76 having different guide planes, thus yielding tool grooves 70 with back surfaces 76 having a variety of slopes or pitches.

In use, after inserting the retractor 10 into an incision and exposing an internal surgical site, the surgeon places the shaft 52 of a tool, such as tap 33, within tool groove 70 of the retractor 10. The tool groove 70 supports the shaft 52 of tap 33, thereby allowing the surgeon to better align the tap 33 with the patient's internal surgical site. If a tap 33 is used, the surgeon may rotate the tap 33 at the surgical site while maintaining the tap 33 in contact with the back surface 76 of tool groove 70, thereby creating a precisely aligned hole for an implant, such as a pedicle screw S.

Figures 11, 11A, 12:
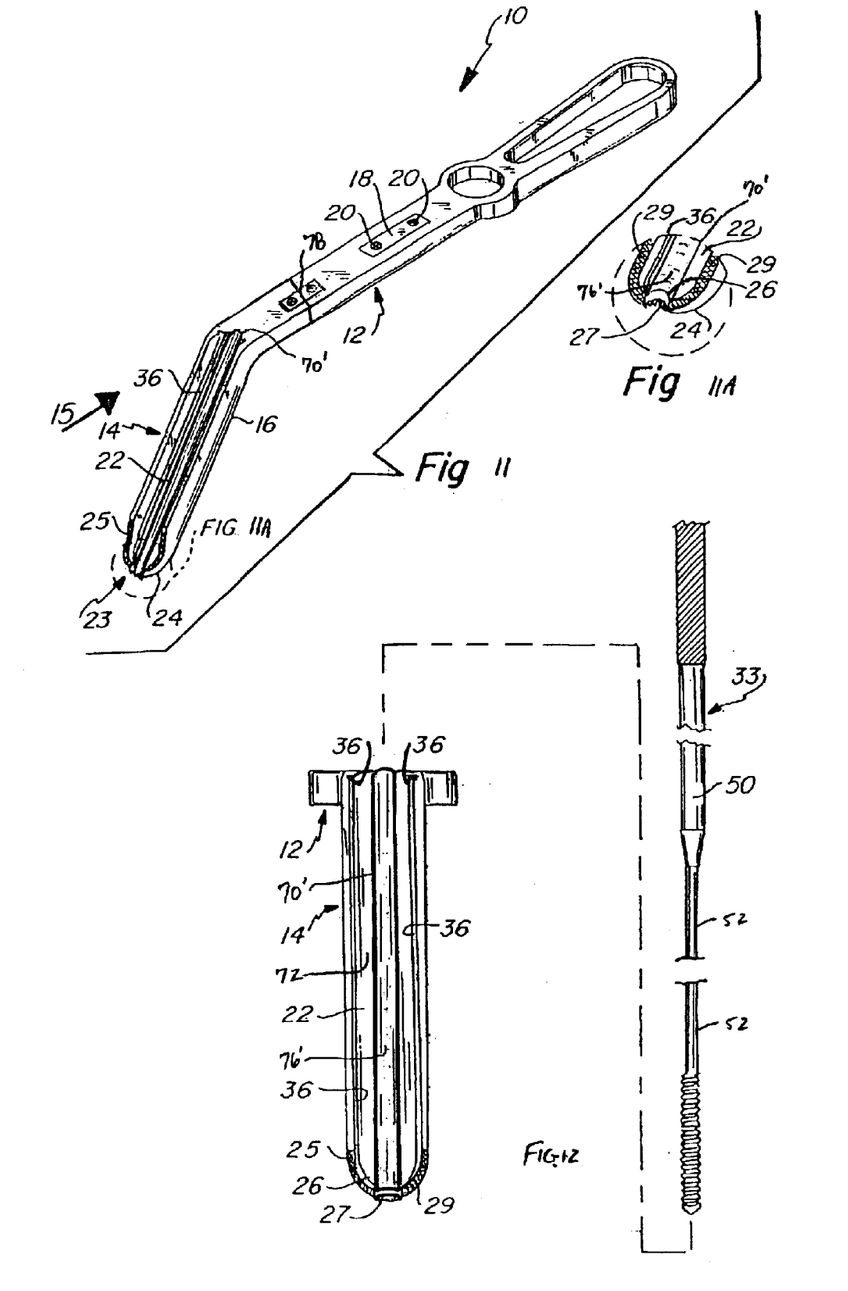
FIG. 11 is a perspective view of a separate embodiment of the present invention having a full-length tool groove.
FIG. 11a is a detail drawing of the rounded tip of the device depicted in FIG. 11.
FIG. 12 is a front elevation view of the retractor depicted in FIG. 11 along arrow 15.

In yet an alternate embodiment shown in FIGS. 11 and 12, retractor 10 may include tool groove 70' that extends the full length of the guide portion 14. FIG. 12 depicts a front elevation view along arrow 15 of the retractor 10 shown in FIG. 11. As with the embodiment shown in FIGS. 9 and 10, the embodiment shown in FIGS. 11 and 12 serves to support the shaft of a tool, such as the shaft 52 of tap 33. Tool groove 70' may maintain a constant depth along the back surface 72 of guide portion 14, or it may vary in depth. Regardless of whether tool groove 70' maintains a constant depth or varies in depth along the back surface 72, the back surface 76' of tool groove 70' provides a plane against which the shaft of a tool maybe used by a surgeon to align the tool with the internal surgical site. Tool groove 70' preferably aligns with opening 26 at the distal end 23 of guide portion 14, as shown in FIG. 11a.

As shown in FIGS. 9–12, the tool groove 70 or 70' may be used with retractors 10 that have means for holding an insert 30, such as grooves 36. Thus, a retractor 10 incorporating a tool groove 70 or 70', can be used in combination with an insert 30, as previously described. As noted above, grooves 36 receive base edges 34 of insert 30 to hold insert 30 within guide channel 22. When an insert 30 is used in combination with a retractor 10 having a tool groove 70 or 70', the insert 30 fits in front of the tool groove 70 or 70'. Alternatively, retractor 10 may not include grooves 36, and can be used without insert 30. Nonetheless, retractor 10 can incorporate tool grooves 70 or 70', and can also be combined with the features at the distal end 23 of guide portion 14, such as the rounded tip 24, opening 26, projections 27, and texturing along the medial surface 29 of the lower medial face 25.

Figure 13:
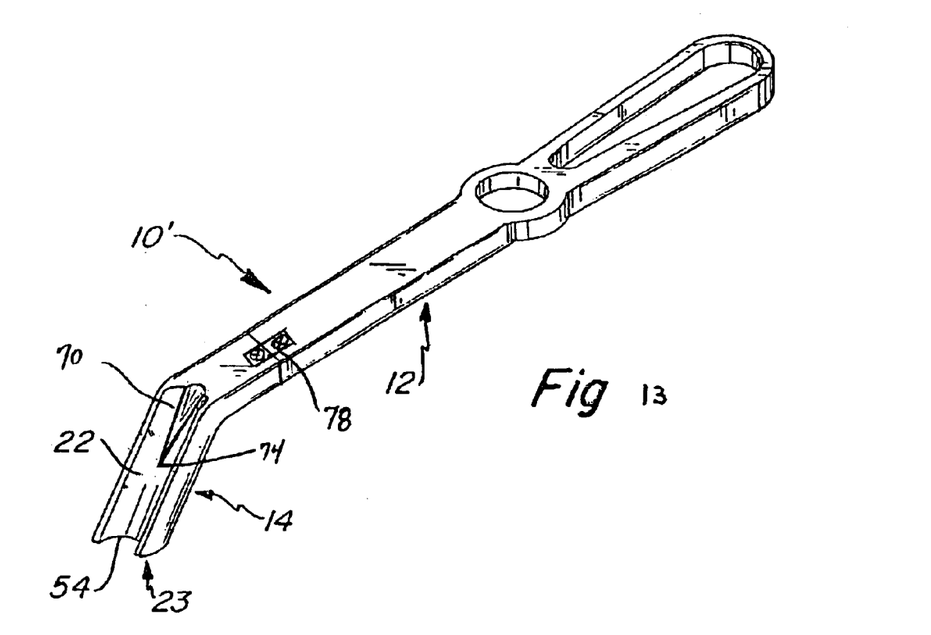
FIG. 13 is a perspective view of a further embodiment of the present invention having a recessed and curved distal tip at its guide portion and a partial-length tool groove.

Referring now to FIG. 13, retractor 10' of FIG. 7 can be modified to include a tool groove 70 within its guide portion 14. That is, a retractor 10' without a rounded tip 24 can have a tool groove 70. This separate embodiment of the present invention incorporates all of the features of the embodiment shown and described in conjunction with FIG. 7, but also includes the partial-length tool groove 70 that can be used to provide a cradle for the shaft of a tool, such as the shaft 52 of tap 33, or the shaft 52 of a medical screwdriver T, as shown in FIG. 6.

Figure 14:
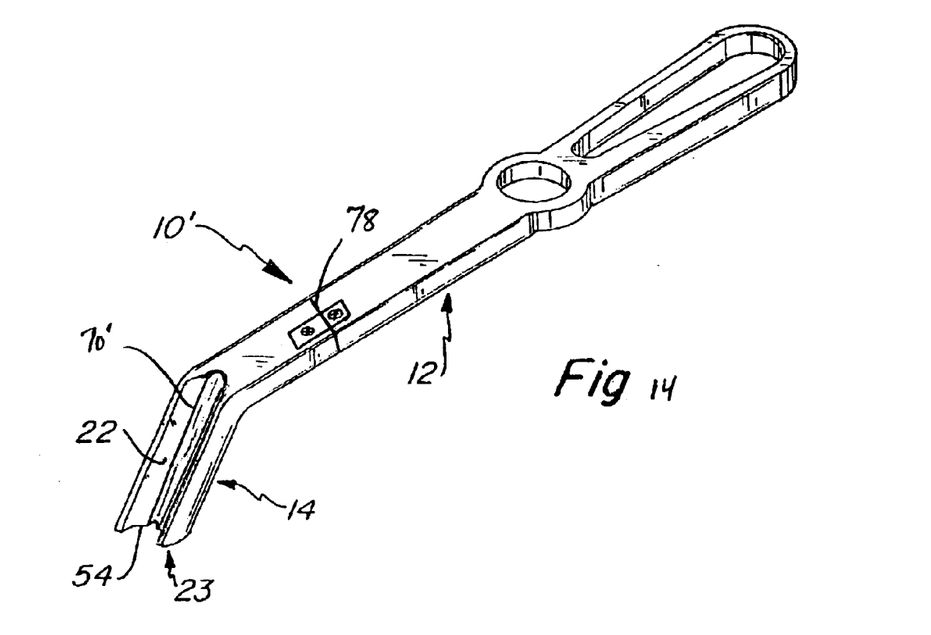
FIG. 14 is a perspective view of a further embodiment of the present invention having a recessed and curved distal tip at its guide portion and a full-length tool groove.

Referring now to FIG. 14, retractor 10' of FIG. 7 can be modified to include a tool groove 70' within its guide portion 14. That is, a retractor 10' without a rounded tip 24 can have a tool groove 70'. This separate embodiment of the present invention incorporates all of the features of the embodiment shown and described in conjunction with FIG. 7, but also includes the full-length tool groove 70' that can be used to provide a cradle for the shaft of a tool, such as the shaft 52 of tap 33.

Figure 15:
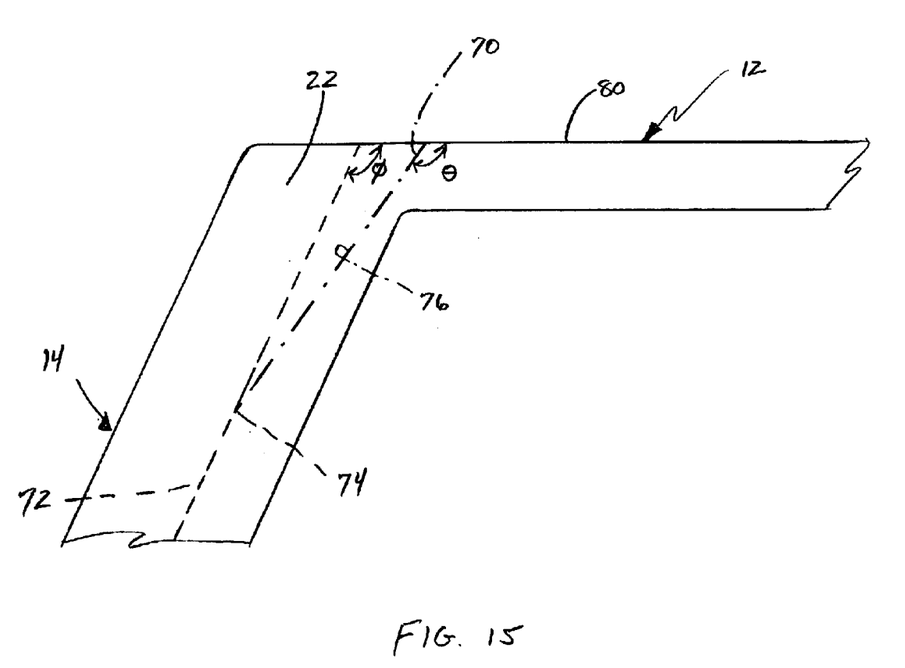
FIG. 15 is an enlarged partial side elevation view of the bend between the handle and the guide portion of a retractor, wherein a partial-length tool groove is shown.

Referring now to FIG. 15, an enlarged partial side elevation view of the transition between the handle 12 and the guide portion 14 is shown. For the example shown in FIG. 15, a retractor having a partial tool groove 70 is depicted, with the tool groove 70 having a back surface 76. The back surface 76 of tool groove 70 intersects a top surface 80 of the handle 12 at an angle θ. Also shown in FIG. 15 is the interior back surface 72 of the guide channel 22. Interior back surface 72 of guide channel 22 forms an angle φ with the top surface of handle 22. Preferably, angle θ is greater than angle φ, such that back surface 76 of tool groove 70 intersects the interior back surface 72 of guide channel 22 at tool groove end 74. Thus, back surface 76 of tool groove 70 serves as an inset and alternately angled surface than that of the interior back surface 72 of guide channel 22.

Figures 16A, 16B, 16C, 16D:
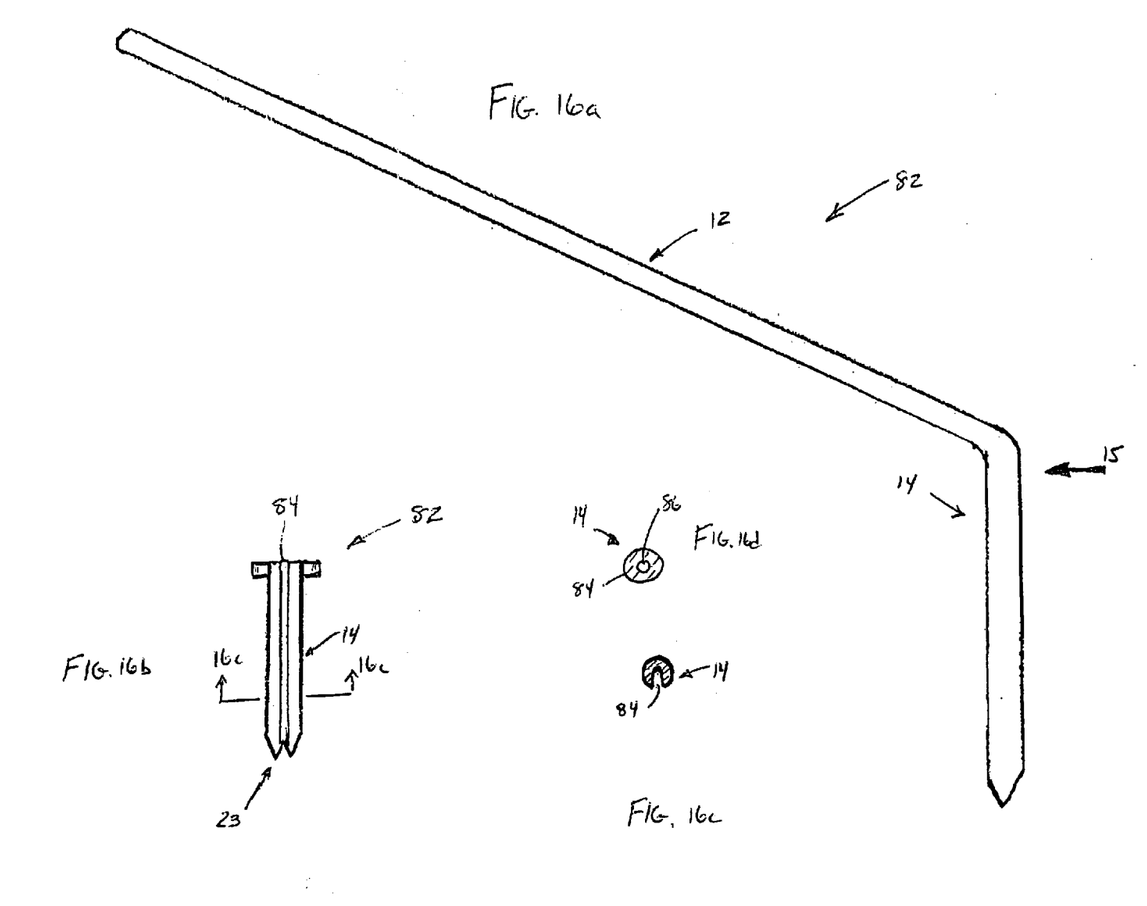
Figure 17A:
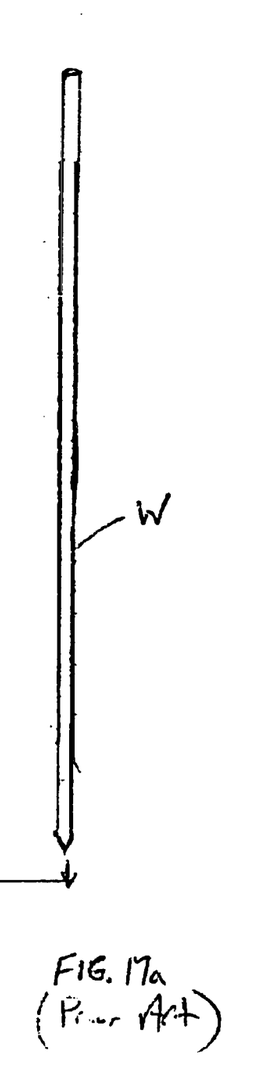
FIG. 17a is a front elevation view of a guide wire.
Figure 17B:
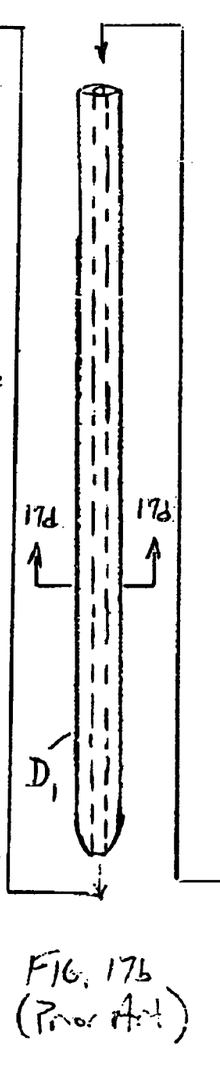
Figure 17C:
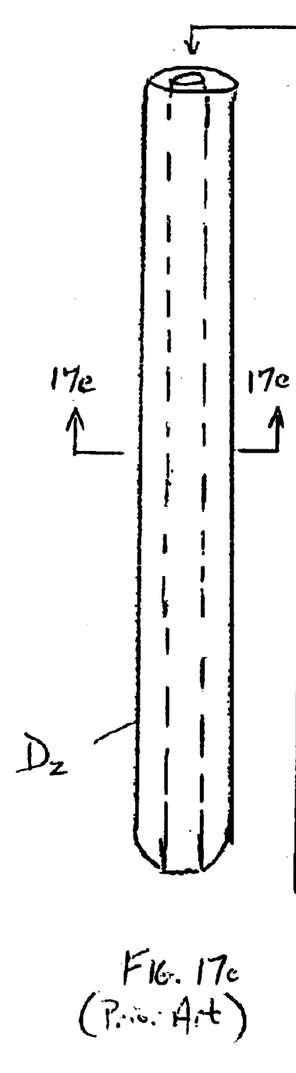
FIG. 17c is a front elevation view of yet a larger cylindrical dilator as compared to the dilator shown in FIG. 17b.
Figures 17D, 17E:
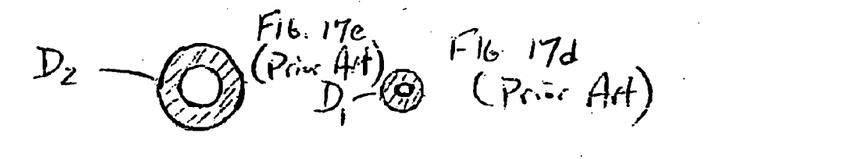
FIG. 17d is a cross-section taken through line 17d—17d of FIG. 17b.
FIG. 17e is a cross-section taken through line 17e—17e of FIG. 17c.

Referring now to FIG. 16a–16c, a separate embodiment of a retractor 82 is shown. Retractor 82 includes a guide portion 14 attached to handle 12, where the guide portion 14 includes slot or wire channel 84, as best seen in FIG. 16c, where the slot or wire channel 84 is suited for placing a guide wire W, as shown in FIG. 17a. Alternatively, as shown in FIG. 16d, the wire channel 84 can be enclosed on its sides with a hole 86 provided through its interior for the guide wire placement. Upon placing a guide wire W, retractor 82 can be withdrawn and subsequent access for tapping and/or pedicle screw placement can be performed by placing a dilator $D_1$ over the guide wire W, or a series of cylindrical dilators $D_1$ and $D_2$ as is shown in FIGS. 17b and 17c. In addition, a separate retractor, such as retractor 10', can then be placed against the dilator and slid into position with the rounded tip 24 of distal end 23 smoothly guiding the muscle from against the dilator to the outer surface of the retractor 10'. Cross sections of the cylindrical dilators shown in FIGS. 17b and 17c are depicted in FIGS. 17d and 17e, respectively.

Retractors 10 or 10' incorporating a tool groove 70 or 70' may be used in combination with an image tracker 60 as previously described. Retractor 82 may also incorporate an image tracker 60.

A plurality of retractors 10 or 10' may be used by a surgeon, wherein the retractor's 10 or 10' possess a variety of tool groove 70 or 70' configurations that allow a surgeon to choose a retractor 10 or 10' with a full-length tool groove 7\0' within guide portion 14 or a partial-length tool groove 70 within guide portion 14, and wherein the tool grooves 70 or 70' may have different depths and pitches. Retractor 82 may be used prior to changing to retractor 10 or 10'.

Alternatively, it is another aspect of the present invention that the guide portion 14 may be detachably connected at a connection point 78 to the handle 12. Guide portion 14 is detachably connected to handle 12 preferably using screws, bolts, a quick connect coupling or some other means, thereby allowing various configurations of guide portions 14 to be interchangeably connected to the handle 12. As a result, various guide portions 14 can be produced having a variety of tool groove 70 or 70' configurations, and the surgeon can attach the desired guide portion 14 deemed appropriate for the given surgical conditions.

All components of the invention and its various embodiments and alternatives described herein are manufactured of a material appropriate for surgical use. For example, the components can be made of stainless steel. However, it is to be understood that other types of materials may also be used, such as titanium or ceramics. Alternatively, it is yet an another aspect of the present invention that the retractor 10 may be manufactured of surgical quality plastics or other disposable materials. This manufacturing aspect allows for relatively inexpensive production of a surgically sterile retractor that can be disposed after each use. A surgeon can pick one or more retractor configurations having different guide portion arrangements for each individual surgery. Alternatively, disposable guide portions 14 can be produced for temporary attachment to a reusable handle12.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A retractor especially adapted for placement of a pedicle screw within a patient, comprising:
    a guide portion having a u-shaped guide channel extending longitudinally therealong, said guide portion including a first end, a second end, and a tool groove inset relative to an interior back surface of the u-shaped guide channel;
    a handle connected angularly with respect to said first end of said guide portion.

2. The device as claimed in claim 1, further comprising means for stabilizing said retractor against a lateral aspect of a facet of a paraspinous musculature of the patient.

3. The device as claimed in claim 1, wherein said second end of said guide portion includes at least one projection extending therefrom for assisting in anchoring the guide portion within the surgical area.

4. The device as claimed in claim 1, wherein said guide portion includes a medial face positioned adjacent said second end thereof, said medial face having a medial service formed with texturing thereon.

5. The device as claimed in claim 1, further comprising grooves formed within said guide channel for receiving at least one base edge of an insert.

6. The device as claimed in claim 1, further comprising an image tracker mounted to said retractor.

7. A retractor for placement of a pedicle screw, comprising:
    a guide portion including a guide channel having an interior back surface and a tool groove having a back surface inset relative to said interior back surface;

an insert configured to fit within said guide channel, said insert having a hollow bore extending lengthwise therethrough, said bore having a diameter sized to accommodate a tool inserted therethrough; and means for stabilizing said insert within said guide channel.

8. The device as claimed in claim 7, wherein said guide channel includes a distal end, said distal end having at least one projection extending therefrom.

9. The device as claimed in claim 7, wherein said guide portion includes a medial face positioned adjacent said second end thereof, said medial face having a medial service formed with texturing thereon.

10. The device as claimed in claim 7, further comprising an image tracker mounted to said retractor.

11. A surgical retractor for guiding implantation of a pedicle screw within a patient's spine, comprising:

a guide portion having a u-shaped guide channel, said u-shaped guide channel sized to accommodate a pedicle screw for implanting in the patient, said guide portion having a distal end and a tool groove at a proximal end, and grooves formed on said u-shaped guide channel adapted to receive an insert; and means for stabilizing the distal end of said guide portion against a lateral aspect of a facet of a paraspinous musculature of the patient.

12. The device as claimed in claim 11, further comprising an elongated insert having at least one base edge configured to fit within the grooves in said guide channel, said insert having an aperture extending lengthwise therethrough.

13. The device as claimed in claim 11, further comprising an image tracker mounted to said retractor.

14. The device as claimed in claim 11, further comprising a semi-circular opening sized to accommodate a pedicle screw at said distal end of said guide portion.

15. The device as claimed in claim 11, further comprising a handle connected to the guide portion.

16. The device as claimed in claim 15, wherein the handle is detachably connected to the guide portion.

17. A method for preparing a vertebra, comprising:

placing a retractor through a skin incision, the retractor including a u-shaped guide channel having a proximal end, a distal end, and a tool groove formed in an interior back surface;

placing a tool through the u-shaped guide channel to position a shaft of the tool within the tool groove; and manipulating the tool while maintaining contact between the shaft and the tool groove.

18. A surgical retractor, comprising:

a guide portion having a u-shaped guide channel adapted to accommodate a pedicle screw for implanting in a patient, said guide portion having a tool groove having a back surface inset relative to a interior back surface of the guide portion; and a handle connected to a first end of the guide portion.

19. The surgical retractor of claim 18, wherein the tool groove extends from a proximal end of the guide portion and tapers toward a distal end of the guide portion.

20. A surgical retractor for guiding implantation of a pedicle screw within a patient's a spine, comprising:

a guide portion having a u-shaped guide channel, said u-shaped guide channel sized to accommodate a pedicle screw for implanting in the patient, said guide portion having proximal and distal ends and a tool groove extending from the proximal end.

21. The surgical retractor of claim 20, wherein the tool groove terminates proximal to the distal end of the guide portion.

* * * * *